United States Patent [19]

Daher et al.

[11] 4,376,118
[45] Mar. 8, 1983

[54] STABLE NONAQUEOUS SOLUTION OF TETRACYCLINE SALT

[75] Inventors: Lawrence J. Daher; George C. Hoss, both of Elkhart, Ind.; Victor A. Raul, Edwardsburg, Mich.

[73] Assignee: Miles Laboratories, Inc., Elkhart, Ind.

[21] Appl. No.: 262,475

[22] Filed: May 19, 1981

Related U.S. Application Data

[63] Continuation-in-part of Ser. No. 194,556, Oct. 6, 1980.

[51] Int. Cl.³ ............................................ A01N 37/18
[52] U.S. Cl. .................................................... 424/227
[58] Field of Search ......................................... 424/227

[56] References Cited

U.S. PATENT DOCUMENTS

| | | |
|---|---|---|
| 3,026,248 | 3/1962 | Noseworthy et al. .............. 424/227 |
| 3,140,232 | 7/1964 | Noseworthy ........................ 424/227 |
| 3,219,529 | 11/1965 | Nash .................................... 424/227 |
| 3,389,174 | 6/1968 | Nash .................................... 424/227 |

Primary Examiner—Nicky Chan
Assistant Examiner—F. T. Moezie
Attorney, Agent, or Firm—Louis E. Davidson

[57] ABSTRACT

Nonaqueous solution of a tetracycline antibiotic salt which is stable upon extended storage comprises a mixture of a tetracycline antibiotic salt, nonaqueous diluent, nonaqueous solvent, and nonaqueous nonionic solubilizer. It preferably also contains an antioxidant and a nonaqueous anionic solubilizer.

3 Claims, No Drawings

4,376,118

STABLE NONAQUEOUS SOLUTION OF TETRACYCLINE SALT

This is a continuation-in-part of U.S. patent application Ser. No. 194,556 filed on Oct. 6, 1980.

BACKGROUND AND PRIOR ART

Tetracycline antibiotics and their salts are well-known therapeutic materials. It has been proposed in the prior art to employ solutions of such tetracycline antibiotics as topical therapeutics for the treatment of various disorders, such as acne vulgaris. Tetracycline antibiotics are known to degrade to form epitetracycline, anhydrotetracycline, epianhydrotetracycline and other degradation products, some of which are unidentified. These degradation products have negligible therapeutic activity. This degradation appears to increase when solutions of tetracycline antibiotics are employed. Solutions of neutral tetracyclines in nonaqueous solvents are disclosed in U.S. Pat. Nos. 3,219,529 and 3,389,174. These references, however, do not disclose or suggest stable nonaqueous solutions of tetracycline antibiotic salts. In fact, these references specifically state that they are not concerned with such salts. An aqueous ethanol solution of tetracycline hydrochloride has been commercially marketed under the tradename "Topicycline", but it is relatively unstable in its solution form.

There is thus a need for a stable nonaqueous solution of tetracycline antibiotic salts.

SUMMARY OF THE INVENTION

In accordance with the present invention, a stable nonaqueous solution of a tetracycline antibiotic salt is provided comprising a mixture of a tetracycline antibiotic salt, nonaqueous diluent, nonaqueous solvent and nonaqueous nonionic solubilizer. Preferably, the solution also contains an antioxidant and a nonaqueous anionic solubilizer.

DESCRIPTION OF THE INVENTION

The tetracycline antibiotic salts used in the present invention are well-known and are readily available from several commercial sources. These salts are, for example, tetracycline hydrochloride, chlortetracycline hydrochloride, oxytetracycline hydrochloride, rolitetracycline hydrochloride, and the like. Tetracycline hydrochloride is the preferred active ingredient.

The nonaqueous solvent can be ethanol, methanol, isopropanol, butanol, N-methyl-2-pyrrolidone or acetone. Ethanol is the preferred solvent.

The nonaqueous diluent which serves as the carrier for the overall composition can be an ester, amide, silicone, triglyceride and the like. Suitable esters include glyceryl triacetate, diisopropyl sebacate, diisopropyl adipate, isopropyl palmitate, isopropyl myristate, lauryl lactate, linear alcohol lactate, decyl oleate, isodecyl oleate, 2-ethylhexyl palmitate, isopropyl linoleate, acetylated monoglyceride, acetyl tributyl citrate, acetyl triethyl citrate, tricyclo hexyl citrate, butyl myristate, promyristyl propionate, dibutyl sebacate, dioctyl adipate, dioctyl succinate, and isobutyl acetate. Suitable amides include acetamide and methylacetamide. Suitable silicones include polydimethyl cyclosiloxane and hexamethyl disiloxane. Suitable triglycerides include fractionated triglycerides of coconut oil origin such as "Neobee M-5" and "Neobee O" (Drew Chemical Corp.).

The nonaqueous solubilizers can be selected from two chemical groupings of materials, the nonionic surfactant type materials and the anionic surfactant type materials. The nonionic surfactant type materials preferably are of a mol. wt. range of 190 to 10,000 and can include polyethylene glycols, methoxy polyethylene glycols, polysorbates, ethylene oxidepropylene oxide block copolymers, sorbitan esters and glycerin. The anionic surfactant type materials can consist of the monovalent or divalent salts of dialkyl sulfosuccinates, acyl lactates and aryl sulfonates. The preferred solubilizers consist of a mixture of a nonionic surfactant type material and an anionic surfactant type material. The most preferred solubilizers consist of a mixture of polyethylene glycol 200 and dioctyl sodium sulfosuccinate.

The antioxidant or antioxidant combination included in this stable solution can consist of ascorbyl palmitate, ascorbic acid, propyl gallate, butylated hydroxytoluene, butylated hydroxyanisole, tertiary butyl hydroquinone, and d-beta, gamma and delta isomers of tocopherol as well as most other commonly known antioxidants.

The stable solution of the present invention generally comprises a mixture of 0.25 to 2 percent tetracycline antibiotic salt, 41 to 88 percent nonaqueous diluent, 4 to 40 percent nonaqueous solvent, 0.3 to 20 percent nonaqueous nonionic solubilizer, 0 to 6 percent nonaqueous anionic solubilizer and 0 to 0.75 percent antioxidant. These percent values are on a weight/weight basis based on the entire solution weight.

A more preferred stable solution of the present invention comprises a mixture of 0.3 to 1.5 percent tetracycline antibiotic salt, 57 to 84 percent nonaqueous diluent, 4 to 30 percent nonaqueous solvent, 2 to 9 percent nonaqueous nonionic solubilizer, 1 to 6 percent nonaqueous anionic solubilizer and 0.03 to 0.2 percent antioxidant.

The most preferred stable solution of the present invention comprises a mixture of 0.5 to 1.25 percent tetracycline antibiotic salt, 60 to 81 percent nonaqueous diluent, 4 to 25 percent nonaqueous solvent, 3 to 9 percent nonaqueous nonionic solubilizer, 1.5 to 4.5 percent nonaqueous anionic solubilizer and 0.1 to 0.2 percent antioxidant.

The solution is conveniently prepared by mixing the ingredients in the following order. The nonaqueous nonionic solubilizer and the nonaqueous anionic solubilizer, if employed, are added to the nonaqueous solvent at ambient room temperature (about 20°-25° C.), and the resulting mixture is stirred until dissolved. The tetracycline antibiotic salt and the antioxidant, if employed, are then added with mixing. The nonaqueous diluent is finally added.

The solutions of the present invention have been stored for extended periods of time at 22° C., 40° C., 50° C. and 60° C. The invention allows the tetracycline antibiotic salt to spontaneously epimerize to an equilibrium condition assumed in the prior art to be about a 1:1 weight ratio of tetracycline to epitetracycline. This ratio is maintained and further tetracycline degradation is inhibited by the overall composition so as to provide a therapeutic effective dosage of tetracycline antibiotic salt for an extended period of time.

The invention is described in further detail in the following examples.

EXAMPLE I

A mixture was prepared having the following composition (Sample A):

| | Percent (weight/weight basis) |
|---|---|
| Tetracycline Hydrochloride | 1.0 |
| Dioctyl Sodium Sulfosuccinate | 4.0 |
| Polyethylene Glycol 200 | 4.0 |
| Ethanol, 200 Proof | 24.4 |
| Glyceryl Triacetate | 22.0 |
| Diisopropyl Sebacate | 44.4 |
| Ascorbyl Palmitate | 0.2 |
| | 100.0 |

A control composition (Sample B) consisting of an aqueous solution of tetracycline salt similar to that employed in the prior art was prepared having the following composition:

| | Percent (weight/weight basis) |
|---|---|
| Tetracycline Hydrochloride | 1.0 |
| Ethanol, 200 Proof | 40.0 |
| Sodium Bisulfite | 0.1 |
| Water | 58.9 |
| | 100.0 |

Appropriate samples of the above two compositions all having an input concentration of 10 mg./ml. tetracycline hydrochloride were stored at 22° C., 40° C., and 50° C. for extended periods. The samples were periodically assayed for tetracycline, epitetracycline and other degradation products. The results are shown in the following Table 1. Though the formulations were initially prepared based on weight/weight percentage amounts of the ingredients, their assay results were reported as weight/volume percentages for convenience. The specific gravities of the compositions were invariably close to 1.000 and any deviation therefrom introduces only errors of no significance into the results.

weight ratio of about 1:1 tetracycline to epitetracycline is spontaneously established in solutions of the salt. Thus for a stable target concentration of say 5 mg./ml., one must have an input level of tetracycline hydrochloride of 10 mg./ml.

Relative stability therefore of 10 mg./ml. input formulas should be calculated as a comparison of the found value versus 5 mg./ml. of tetracycline hydrochloride. The composition of the present invention (Sample A) of Example 1 shows a retention of:

$\frac{5.01}{5} \times 100 = 100\%$ tetracycline hydrochloride at 26 wks. 22° C.

$\frac{4.65}{5} \times 100 = 93\%$ tetracycline hydrochloride at 52 wks. 22° C.

$\frac{4.99}{5} \times 100 = 100\%$ tetracycline hydrochloride at 8 wks. 40° C.

$\frac{4.85}{5} \times 100 = 97\%$ tetracycline hydrochloride at 13 wks. 40° C.

$\frac{4.77}{5} \times 100 = 95\%$ tetracycline hydrochloride at 4 wks. 50° C.

$\frac{4.37}{5} \times 100 = 87\%$ tetracycline hydrochloride at 8 wks. 50° C.

Comparatively the control composition of the prior art aqueous solution (Sample B) has a retention of:

$\frac{4.16}{5} \times 100 = 83\%$ tetracycline hydrochloride at 26 wks. 22° C.

$\frac{3.47}{5} \times 100 = 69\%$ tetracycline hydrochloride at 52 wks. 22° C.

$\frac{3.08}{5} \times 100 = 62\%$ tetracycline hydrochloride at 8 wks. 40° C.

$\frac{2.79}{5} \times 100 = 56\%$ tetracycline hydrochloride at 4 wks. 50, C.

TABLE 1

| | | Assayed Concentration (mg./ml.) After Indicated Storage Conditions | | | | | |
|---|---|---|---|---|---|---|---|
| | | 22° C. | | 40° C. | | 50° C. | |
| | Start | 26 wk. | 52 wk. | 8 wk. | 13 wk. | 4 wk. | 8 wk. |
| | | Sample A | | | | | |
| Tetracycline HCl | 9.44 | 5.01 | 4.65 | 4.99 | 4.85 | 4.77 | 4.37 |
| Epitetracycline HCl | 0.49 | 5.08 | 5.63 | 5.02 | 4.73 | 4.24 | 4.34 |
| Total | 9.93 | 10.09 | 10.28 | 10.01 | 9.58 | 9.01 | 8.71 |
| Other Degradation Products (Combined anhydrotetracycline and epianhydrotetracycline) | 0.05 | 0.10 | 0.17 | 0.28 | 0.46 | 0.47 | 1.12 |
| Total Assayable Products | 9.98 | 10.19 | 10.45 | 10.29 | 10.04 | 9.48 | 9.83 |
| | | Sample B | | | | | |
| Tetracycline HCl | 9.81 | 4.16 | 3.47 | 3.08 | | 2.79 | 0 |
| Epitetracycline HCl | 0.56 | 5.32 | 4.84 | 3.98 | | 3.29 | 2.05 |
| Total | 10.37 | 9.48 | 8.31 | 7.06 | | 6.08 | 2.05 |
| Other Degradation Products | — | 0.18 | 0.37 | 0.69 | | 0.75 | 1.71 |
| Total Assayable Products | 10.37 | 9.66 | 8.68 | 7.75 | | 6.83 | 3.76 |

Evaluation of the above data must take into consideration the previously mentioned epimerization reaction of tetracycline antibiotic salts wherein an equilibrium $\frac{0}{5} \times 100 = 0\%$ tetracycline hydrochloride at 8 wks. 50° C.

It can thus be seen from the above data that the composition of the present invention is considerably more stable on extended storage than a typical comparable prior art composition.

Additional examples of varying compositions within the scope of the present invention are listed in the following Table 2. In addition, chemical stability data on a number of these formulations are given in Table 3.

TABLE 2

Additional Examples of Formulas Of The Invention
(Percents on weight/weight basis)

| Examples | 2 | 3 | 4 | 5 | 6 | 7 | 8 | 9 |
|---|---|---|---|---|---|---|---|---|
| Tetracycline Antibiotic Salt | | | | | | | | |
| Tetracycline Hydrochloride | 1.0 | 0.25 | 0.5 | 2.0 | 1.0 | 0.5 | 1.0 | 0.5 |
| Nonaqueous Diluent | | | | | | | | |
| Diisopropyl Sebacate | 44.08 | 51.23 | 46.88 | 19.8 | 34.95 | 36.5 | 52.94 | 64.56 |
| Glyceryl Triacetate | 22.4 | 22.0 | 22.1 | 22.1 | 22.0 | 22.1 | 22.28 | 22.0 |
| Nonaqueous Solvent | | | | | | | | |
| Ethanol | 24.42 | 24.42 | 24.42 | 40.0 | 2.48 | 40.0 | 14.0 | 8.0 |
| Acetone | | | | | 24.82 | | | |
| Nonaqueous Anionic Solubilizer | | | | | | | | |
| Dioctyl Sodium Sulfosuccinate | 2.0 | 0.5 | 1.0 | 6.0 | 3.68 | 0.5 | 3.68 | 1.84 |
| Nonaqueous Nonionic Solubilizer | | | | | | | | |
| Polyethylene Glycol-200 | 6.0 | 1.5 | | 10.0 | 7.0 | 0.3 | 6.0 | 3.0 |
| Methoxy Polyethylene Glycol-350 | | | 5.0 | | | | | |
| Glycerin | | | | | 4.0 | | | |
| Antioxidant | | | | | | | | |
| Ascorbic Acid | 0.1 | 0.1 | 0.1 | 0.1 | | 0.1 | | 0.1 |
| Ascorbyl Palmitate | | | | | | | 0.1 | |
| Tocopherol Concentrate, Mixed 50% | | | | | 0.07 | | | |
| TOTAL PERCENT | 100.0 | 100.0 | 100.0 | 100.0 | 100.0 | 100.0 | 100.0 | 100.0 |

| Examples | 10 | 11 | 12 | 13 | 14 | 15 | 16 | 17 |
|---|---|---|---|---|---|---|---|---|
| Tetracycline Antibiotic Salt | | | | | | | | |
| Tetracycline Hydrochloride | 0.5 | 1.0 | 1.0 | 1.0 | 1.0 | 0.5 | 1.0 | 1.0 |
| Nonaqueous Diluent | | | | | | | | |
| Diisopropyl Sebacate | 65.56 | 44.76 | 44.38 | | 37.38 | 49.98 | 42.38 | 42.48 |
| Glyceryl Triacetate | 22.0 | 22.0 | 22.1 | 66.8 | 22.1 | 22.0 | 22.1 | 22.0 |
| Nonaqueous Solvent | | | | | | | | |
| Ethanol | 4.0 | 24.42 | 24.42 | 24.42 | 24.42 | 24.42 | 24.42 | 24.42 |
| Nonaqueous Anionic Solubilizer | | | | | | | | |
| Dioctyl Sodium Sulfosuccinate | 1.84 | 3.68 | 4.0 | 3.68 | | 2.0 | 2.0 | 4.0 |
| Nonaqueous Nonionic Solubilizer | | | | | | | | |
| Polyethylene Glycol-200 | 6.0 | 4.0 | 4.0 | 4.0 | 15.0 | | 8.0 | 6.0 |
| Polyoxypropylene Glycol F68 | | | | | | 1.0 | | |
| Antioxidant | | | | | | | | |
| Ascorbic Acid | | | 0.1 | | 0.1 | 0.1 | 0.1 | |
| Ascorbyl Palmitate | 0.1 | | | 0.1 | | | | |
| Tocopherol Concentrate, Mixed 50% | | 0.14 | | | | | | 0.10 |
| TOTAL PERCENT | 100.0 | 100.0 | 100.0 | 100.0 | 100.0 | 100.0 | 100.0 | 100.0 |

| Examples | 18 | 19 | 20 | 21 | 22 | 23 | 24 |
|---|---|---|---|---|---|---|---|
| Tetracycline Antibiotic Salt | | | | | | | |
| Tetracycline Hydrochloride | 1.0 | 1.0 | 1.0 | 1.0 | 1.0 | 1.0 | 1.0 |
| Nonaqueous Diluent | | | | | | | |
| Diisopropyl Sebacate | 41.83 | 42.53 | 42.56 | 58.22 | 30.18 | | 31.98 |
| Diisopropyl Adipate | | | | | | 42.38 | |
| Glyceryl Triacetate | 22.0 | 22.0 | 22.0 | 22.0 | 22.4 | 22.1 | 22.5 |
| Nonaqueous Solvent | | | | | | | |
| Ethanol | 24.42 | 24.42 | 24.42 | 8.0 | 24.42 | 24.42 | 24.42 |
| Nonaqueous Anionic Solubilizer | | | | | | | |
| Dioctyl Sodium Sulfonsuccinate | 4.0 | 4.0 | 4.0 | 3.68 | 2.0 | 2.0 | |
| Nonaqueous Nonionic Solubilizer | | | | | | | |
| Polyethylene Glycol-200 | 6.0 | 6.0 | 6.0 | 7.0 | | 8.0 | 10.0 |
| Methoxy Polyethylene Glycol-350 | | | | | 20.0 | | |
| Propylene Glycol | | | | | | | 10.0 |
| Antioxidant | | | | | | | |
| Ascorbic Acid | 0.75 | | | | | 0.1 | |
| Ascorbyl Palmitate | | 0.05 | | 0.1 | | | 0.1 |
| Tocopherol Concentrate, Mixed 50% | | | 0.02 | | | | |
| TOTAL PERCENT | 100.0 | 100.0 | 100.0 | 100.0 | 100.0 | 100.0 | 100.0 |

TABLE 3

Chemical Stability of Tetracycline Hydrochloride.
Values were derived from the following equation:
Percent tetracycline HCl retained =
$$\frac{\% \text{ w/v of TC.HCl} \times 100}{50\% \text{ of initial conc. of TC.HCl}}$$

| Example | 22°C 26 wk | 22°C 52 wk | 40°C 8 wk | 40°C 13 wk | 50°C 4 wk | 50°C 8 wk | 60°C 2 wk | 60°C 4 wk | 70°C 2 wk |
|---|---|---|---|---|---|---|---|---|---|
| 2 | 98.2 | 86.8 | 86.0 | 85.4 | 90.6 | 80.2 | | | |
| 3 | 100.0 | | 99.2 | 100.0 | 98.4 | 91.2 | | | |
| 4 | 95.2 | 86.8 | 90.4 | 84.8 | 97.2 | 89.2 | | | |
| 5 | 87.3 | | 87.8 | 91.8 | 79.2 | 75.0 | | | |
| 6 | | | | | | | | 69.0 | |
| 7 | 100.0 | 83.2 | 84.0 | 90.4 | 88.4 | 76.0 | | | |
| 8 | | | | | | | | | 53.2 |
| 11 | | | | | 92.2 | | 95.6 | 63.2 | 24.8 |
| 12 | 94.0 | 97.4 | 100.0 | 92.6 | 93.4 | 93.8 | | | |
| 13 | | | | | | | 87.8 | | |
| 14 | 83.8 | 80.4 | 81.6 | 78.4 | 85.6 | 66.4 | | | |
| 15 | 100.0 | 93.6 | 99.6 | 100.0 | 100.0 | 92.4 | | | |
| 17 | | | | | | 86.0 | 100.0 | | |
| 18 | | | | | | | 98.2 | | |
| 19 | | | | | | | 100.0 | | |
| 20 | | | | | | | 100.0 | | |
| 22 | | 79.4 | | | | | | | |

It can be seen from the above data that compositions of the present invention are relatively quite stable for extended storage periods even at elevated temperatures.

Therapeutic utility for the stable solutions of the present invention is shown in the following example.

EXAMPLE 25

A solution was prepared having the following composition with contents expressed as weight/volume percent based on total solution volume:

| Ingredient | Concentration |
|---|---|
| Tetracycline HCl | 1.00 |
| Dioctyl Sodium Sulfosuccinate | 2.00 |
| Ethanol 200 Proof | 24.42 |
| Ascorbic Acid | 0.10 |
| Polyethylene Glycol 200 | 6.0 |
| Glyceryl Triacetate | 22.10 |
| Diisopropyl Sebacate | 44.38 |

Eight 0.1 ml. portions of the above solution were separately applied to eight 1.4 cm dia. sections of cadaver leg skin. The solution portions were applied to the surface of the epidermis. As a control, eight 0.1 ml. portions of an aqueous solution of tetracycline hydrochloride available commercially under the trade name "Topicycline" were also separately applied to eight 1.4 cm. dia. sections of cadaver leg skin. The solution portions were left in contact with the skin for 16 hours and the epidermis was washed with soap and water. The epidermis was then separated from the corium layer of the skin. A 6 mm. dia. punch biopsy sample of each corium layer was then obtained and transferred to a growth plate inoculated with *Propionibacterium acnes* microorganisms. The resulting plates were then incubated for five days under anaerobic conditions at room temperature. The resulting organism growth was then observed. Any inhibition of growth around the corium disc will indicate antibiotic therapeutic activity. The inhibition is expressed as the radius of area having no organism growth. The portions of samples of the solution of the present invention all had inhibition areas with radii from 9 to 12 mm. None of the prior art samples had any inhibition areas. These results show that the solution of the present invention can penetrate through the epidermis and can retain desirable therapeutic acitivity.

The above data on the tetracycline, epitetracycline and degradation products (such as anhydrotetracycline) of the various compositions were obtained using a column chromatography-spectrophotometric method generally described in the Journal of Pharmaceutical Sciences, Vol. 59, pp. 1480–1482 (1970) or a modification thereof. The modified assay procedure is as follows:

COLUMN CHROMATOGRAPHY SPECTROPHOTOMETRIC PROCEDURE

Several assay solutions are prepared.

1. Butanol-chloroform: mix 100 ml. n-butyl alcohol with 100 ml. chloroform.

2. EDTA: dissolve 37.2±0.1 g. (ethylene dinitrilo) tetraacetic acid disodium salt in about 800 ml. water. Adjust pH to 6.5±0.5 with conc. ammonium hydroxide. Dilute to 1 l. with water.

3. PEG 400: to 80 ml. glycerin add sufficient polyethylene glycol 400 to make 100 ml. Mix well.

4. Buffer: to a 500 ml. volumetric flask add 25.0 ml. PEG 400 solution and dilute to volume with EDTA solution.

5. EtOAc: shake 125 ml. ethyl acetate with 5 ml. water and about 3 g. (ethylene dinitrilo) tetraacetic acid disodium salt until saturated. Filter through Whatman No. 1 filter paper.

6. Alkaline MeOH: dilute 5.0 ml. conc. ammonium hydroxide to 100 ml. with anhydrous methyl alcohol.

7. Tetracycline standard: weigh accurately about 70 mg. tetracycline hydrochloride and quantitatively transfer to a 100 ml. volumetric flask. Add 10 ml. methyl alcohol. After dissolution of the tetracycline, dilute to volume with chloroform.

The diatomaceous earth to be used as the chromatographic column support is prepared by adding about 400 ml. water and 400 ml. hydrochloric acid to about 200 g. Johns-Manville Celite 545 and stirring about 15 min. The solids are then filtered and washed with water until the washings are neutral. The Celite is then mixed with about 250 ml. ethyl acetate, and 250 ml. methyl alcohol for 15 min. The solids are then filtered and vacuum dried at 60° C.

The chromatographic column is prepared by mixing 20 ml. buffer with 40 g. diatomaceous earth (support) until the support is uniformly coated. A disc of Whatman 541 filter paper is placed at the bottom of a 1.3×45 cm. glass column fitted with a Teflon stopcock at its lower end. Weigh 8±0.1 g. support and add to the column in three portions. After each portion addition, settle the support by firmly tapping the column on a padded bench top from a height of 5–10 cm. Then lightly tamp the support surface with a glass tamping rod having a diameter slightly less than the internal diameter of the column. The final support height in the column should be about 10.5–11.5 cm.

A sample solution for assay is prepared by accurately transferring a portion of sample equivalent to 15–20 mg. tetracycline (e.g., 2.0 ml. for 1% solution) to a 25 ml. volumetric flask. Dilute to volume with buffer. Transfer exactly 1.0 ml. sample solution to a 50 ml. beaker. Mix thoroughly with 2.0±0.1 g. support. Quantitatively transfer the support to the column. Wash the beaker with 0.5±0.1 g. support and add to the column. Tamp well. Add 20 ml. EtOAc solution to the top of the column. Collect exactly 10 ml. eluate in a 10 ml. volumetric flask. This Cut 1 will contain the degradation products, such as anhydrotetracycline. Change to a 25 ml. graduated cylinder for the Cut 2 receiver. When the solvent level in the column drops to the level of the support, add 60 ml. chloroform to the column. Collect exactly 20 ml. eluate (Cut 2). Replace the receiver with a 50 ml. volumetric flask. Collect the remaining chloroform eluate (Cut 3) until the chloroform level in the column drops to the level of the support. Replace the 50 ml. volumetric flask with a 10 ml. graduated cylinder. Add 40 ml. butanol-chloroform to the column and collect 8.0 ml. eluate (Cut 4). Tetracycline is in Cuts 2, 3 and 4. Add Cut 4 to Cut 3. Collect the remaining eluate in a 50 ml. graduated cylinder. This final Cut 5 contains the epitetracycline.

The absorbance of Cut 1 at 438 nm in a 1 cm cell is determined versus chloroform. The absorbance of standard tetracycline is obtained by transferring exactly 2.0 ml. standard tetracycline solution to a 100 ml. volumetric flask, adding about 90 ml. chloroform and 2.0 ml. alkaline MeOH, mixing and diluting to volume with chloroform. The absorbance of the resulting solution within 10 min. at 366 nm in a 1 cm. cell versus chloroform is then measured. Cut 2 is mixed well with 2.0 ml. alkaline MeOH and its absorbance is measured in a 1 cm. cell within 10 min. at 366 nm. versus chloroform. Cut 3 is mixed with 2.0 ml. alkaline MeOH and diluted to volume with chloroform. Its absorbance is measured within 10 min. at 366 nm. in a 1 cm. cell versus chloroform. Mix Cut 5 with 2.0 ml. alkaline MeOH and record the final volume. Its absorbance is measured within 10 min. at 366 nm. in a 1 cm. cell versus chloroform.

The concentrations of anhydrotetracycline, tetracycline and epitetracycline are calculated as follows:

Anhydrotetracycline (ATC)

$$\frac{\text{Abs. Cut 1}}{0.0185} \times \frac{\text{vol. Cut 1}}{\text{sample vol.}} \times \frac{\text{sample}}{\text{dilution}} \times \frac{1}{1000} = \text{mg ATC/ml.}$$

mg. ATC/ml./theoretical tetracycline, mg./ml. × 100 = % ATC

Tetracycline (TC)

$$\frac{\text{Abs. Cut 2}}{\text{Abs. Std. TC}} \times \frac{\text{wt.std.,mg.}}{100 \text{ ml.}} \times \frac{2 \text{ ml.}}{100 \text{ ml.}} \times \quad \text{(A)}$$

$$\frac{\text{vol. Cut 2}}{\text{sample vol.}} \times \frac{\text{sample}}{\text{dilution}} = \text{mg. TC/ml.}$$

$$\frac{\text{Abs. Cut 3}}{\text{Abs. Std. TC}} \times \frac{\text{wt.std.,mg.}}{100 \text{ ml.}} \times \frac{2 \text{ ml.}}{100 \text{ ml.}} \times \quad \text{(B)}$$

$$\frac{\text{vol. Cut 3}}{\text{sample vol.}} \times \frac{\text{sample}}{\text{dilution}} = \text{mg. TC/ml.}$$

A + B/theoretical TC, mg./mg. × 100 = % TC

Epitetracycline (ETC)

$$\frac{\text{Abs. Cut 5}}{\text{Abs. Std. TC}} \times \frac{\text{wt.std.,mg.}}{100 \text{ ml.}} \times \frac{2 \text{ ml.}}{100 \text{ ml.}} \times \frac{\text{vol. Cut 5}}{\text{sample vol.}} \times$$

$$\frac{\text{sample}}{\text{dilution}} = \text{mg. ETC/ml.}$$

-continued mg.ETC/ml./theoretical TC, mg./ml. × 100 = % ETC

If % ATC+% TC+% ETC is less than 90%, the assay should be repeated to confirm the results.

Subsequently, a different analytical procedure was employed. This reversed phase high pressure liquid chromatography procedure is as follows.

REVERSED PHAE HPLC

Several assay solutions are prepared.

1. Perchloric acid stock solution: dilute 43 ml. 70% perchloric acid to 1 liter with water.
2. Mobile Phase A: dilute 100 ml. perchloric acid stock solution to 1 liter with water.
3. Mobile Phase B: dilute 100 ml. perchloric acid stock solution to 1 liter with HPLC grade acetonitrile.
4. Tetracycline Standard, Stock Solution: Accurately weigh about 12 mg. USP reference tetracycline and quantitatively transfer to a 50 ml. volumetric flask. Dissolve in and dilute to volume with methanol. Store in a freezer.
5. Anhydrotetracycline Standard, Stock Solution: Accurately weigh about 5 mg. European Pharmacopia reference standard anhydrotetracycline and quantitatively transfer to a 100 ml. volumetric flask. Dissolve in and dilute to volume with methanol. Store in a freezer.
6. Working Standard: On the day of use mix 1 ml. each of tetracycline and anhydrotetracycline standard stock solutions.

The equipment employed for the assay is well-known HPLC apparatus equipped with a 10 microliter loop injector, column oven, gradient generator and computing integrator. The accessory chromatographic column is 4×250 mm. containing Lichrosorb RP-8, 10 micron. The initial composition of the liquid applied to the column is 89 vol. percent Mobile Phase A and 11 vol. percent Mobile Phase B. The final composition of the liquid applied to the column is 29 vol. percent Mobile Phase A and 71 vol. percent Mobile Phase B. The gradient rate is 3 vol. percent/min. and the flow rate is 2 ml./min. The temperature is 40° C., the detection wavelength is 275 nm. and the sensitivity is 0.1 AUFS.

A sample solution for assay is prepared by transferring 1.0 ml. sample to a 25 ml. volumetric flask and diluting to volume with methanol. Filter all samples and standards through Whatman GF/F filter paper prior to injection. Make duplicate injections of the working standard and single injections of each sample. After each injection immediately start the gradient and the integrator. Allow at least 8 min. at initial conditions, for equilibration, after each gradient run before making the next injection. The approximate retention times are as follows:

| | |
|---|---|
| Epitetracycline | 480 seconds |
| Tetracycline | 540 seconds |
| Epianhydrotetracycline | 810 seconds |
| Anhydrotetracycline | 860 seconds |

The concentrations of tetracycline, epitetracycline, anhydrotetracycline and epianhydrotetracycline are calculated as follows:

Tetracycline (TC)

-continued $$\frac{\text{Peak area sample TC} \times \text{wt. TC Std.(gm.)} \times 25 \times 100}{\text{Peak area STd. TC} \times 50 \text{ ml.} \times 2 \times 1 \text{ ml.}} = \% \text{ TC (w/v)}$$

Epitetracycline (ETC)

$$\frac{\text{Peak area sample ETC} \times \text{wt. TC std.(gm.)} \times 25 \text{ ml.} \times 100 \times 1.293}{\text{Peak area std. TC} \times 50 \text{ ml.} \times 2 \times 1 \text{ ml.}} = \% \text{ ETC (w/v)}$$

Anhydrotetracycline (ATC)

$$\frac{\text{Peak area sample ATC} \times \text{wt. ATC std. (gm.)} \times 25 \text{ ml.} \times 100}{\text{Peak area std. ATC} \times 100 \times 2 \times 1 \text{ ml.}} = \% \text{ ATC (w/v)}$$

Epianhydrotetracycline (EATC)

$$\frac{\text{Peak area sample EATC} \times \text{wt. ATC std. (gm.)} \times 25 \text{ ml.} \times 100 \times 1.081}{\text{Peak area std. ATC} \times 100 \text{ ml.} \times 2 \times 1 \text{ ml.}} = \% \text{ EATC (w/v)}$$

Both USP Reference Standard Tetracycline and European Pharmacopia Reference Standard Anhydrotetracycline may contain small amounts of the corresponding epimer. When this occurs, a corrected peak area (P.A.) must be used. This is determined as follows.

Corrected P.A.Std. TC=P.A.Std.
TC+1.293×P.A.ETC,
Corrected P.A.Std. ATC=P.A.Std.
ATC+1.081×P.A.EATC.

While employing the above HPLC procedure, it was found that the equilibrium weight ratio of tetracycline:epitetracycline is actually about 3:4. Therefore, whenever this ratio is maintained over extended storage periods, it indicates a stable tetracycline composition.

Additional examples of varying compositions within the scope of the present invention are listed in the following Table 4. In addition, chemical stability data on several of these formulations are given in Tables 5 and 6. The HPLC assay procedure was used to measure the concentrations of tetracycline and epitetracycline shown in Tables 5 and 6.

TABLE 5

ESTABLISHMENT OF THE TETRACYCLINE HYDROCHLORIDE:EPITETRACYCLINE HYDROCHLORIDE
Epimerization Ratio Using Long Term 22° C. Storage Data

| Example | mg./ml. | Storage Time | | | |
|---|---|---|---|---|---|
| | | 20 wks. | 26 wks. | 104 wks. | 112 wks. |
| 11 | TC.HCl.* | 4.24 | | | |
| | ETC.HCl.** | 5.50 | | | |
| | Ratio | 0.7709 | | | |
| 21 | TC.HCl. | | 4.32 | 4.40 | |
| | ETC.HCl. | | 5.91 | 6.07 | |
| | Ratio | | 0.7310 | 0.7249 | |
| 25 | TC.HCl. | | | | 3.99 |
| | ETC.HCl. | | | | 5.62 |
| | Ratio | | | | 0.7100 |
| 26 | TC.HCl. | | | 4.26 | |
| | ETC.HCl. | | | 5.40 | |
| | Ratio | | | 0.7900 | |
| 30 | TC.HCl. | | | | 4.29 |
| | ETC.HCl. | | | | 5.39 |
| | Ratio | | | | 0.7959 |
| 31 | TC.HCl. | 4.47 | | | |
| | ETC.HCl. | 6.08 | | | |
| | Ratio | 0.7352 | | | |

\* = Tetracycline hydrochloride
\*\* = Epitetracycline hydrochloride
This data supports a nominal 3:4 tetracycline hydrochloride:epitetracycline hydrochloride epimerization ratio, at 22° C., for a range of compositions illustrative of our invention.

TABLE 4

ADDITIONAL EXAMPLES OF FORMULAS OF THE INVENTION
(PERCENTS ON WEIGHT/WEIGHT BASIS)

| Examples: | 26 | 27 | 28 | 29 | 30 | 31 | 32 | 33 |
|---|---|---|---|---|---|---|---|---|
| Tetracycline Antibiotic Salt | | | | | | | | |
| Tetracycline Hydrochloride | 1.0 | 1.0 | 1.0 | 1.0 | 1.0 | 1.0 | 1.0 | 1.0 |
| Nonaqueous Diluent | | | | | | | | |
| Diisopropyl Sebacate | 66.48 | | | 66.38 | 42.38 | 39.7 | 44.2 | 39.7 |
| Diisopropyl Adipate | | | 66.48 | | | | | |
| Glyceryl Triacetate | | | | | 22.1 | 22.0 | 22.0 | 22.0 |
| Promyristyl Propionate | | 66.48 | | | | | | |
| Nonaqueous Solvent | | | | | | | | |
| Ethanol | 24.42 | 24.42 | 24.42 | 24.42 | 24.42 | 24.42 | 24.42 | 24.42 |
| N—methyl-2-pyrrolidone | | | | | | | 0.5 | 5.0 |
| Nonaqueous Anionic Solubilizer | | | | | | | | |
| Dioctyl Sodium Sulfosuccinate | 4.0 | 4.0 | 4.0 | 4.0 | 6.0 | 3.68 | 3.68 | 3.68 |
| Nonaqueous Nonionic Solubilizer | | | | | | | | |
| Polyethylene Glycol-200 | 4.0 | 4.0 | 4.0 | 4.0 | 4.0 | | 4.0 | 4.0 |
| Methoxy Polyethylene Glycol-350 | | | | | | 9.0 | | |
| Antioxidant | | | | | | | | |
| Ascorbic Acid | 0.1 | 0.1 | 0.1 | 0.1 | 0.1 | 0.2 | | |
| Ascorbyl Palmitate | | | | | | | 0.2 | 0.2 |
| Tertiary Butyl Hydroquinone | | | | 0.1 | | | | |
| TOTAL PERCENTS | 100.0 | 100.0 | 100.0 | 100.0 | 100.0 | 100.0 | 100.0 | 100.0 |

TABLE 6

| | *EQUIVALENT PERCENTAGE TETRACYCLINE HYDROCHLORIDE RETAINED | | | | | | | | | | | |
|---|---|---|---|---|---|---|---|---|---|---|---|---|
| | 22° C. | | | | | | 40° C. | | 50° C. | | | 60° C. |
| Example | 13 wk. | 20 wk. | 26 wk. | 52 wk. | 104 wk. | 112 wk. | 8 wk. | 13 wk. | 4 wk. | 8 wk. | 13 wk. | 2 wk. | 4 wk. |
| 10 | | | | | | | | 92.4 | 110.1 | 84.5 | 76.1 | 99.9 | |
| 11 | | 98.9 | | | | | 106.9 | | 107.6 | | | 111.5 | 73.7 |
| 21 | | | 100.8 | 102.7 | | | | 96.6 | 107.9 | 88.0 | 86.1 | | |
| 25 | | | | | | 93.1 | | | | | | | |
| 26 | | | | | 99.4 | | | | | | | | |
| 30 | | | | | | 100.1 | | | | | | | |
| 31 | | | 104.3 | | | | | 97.3 | | 98.5 | 81.0 | | |
| 32 | | | | | | | | | | | | 92.6 | |
| 33 | | | | | | | | | | | | 89.6 | |
| **TOPI-CYCLINE® | | | 72.4 | 63.1 | | | | 41.9 | | | 11.5 | | |

*The table values were derived as follows: assay value in $$\frac{mg}{ml} \times \frac{1 \text{ gm.}}{1000 \text{ mg.}} \times \frac{7}{3} \times 100 = \text{Equivalent percentage of TC.HCl. retained.}$$

**TOPICYCLINE is supplied as an equilibrium powder mixture of tetracycline hydrochloride & epitetracycline hydrochloride hence, there is no spontaneous epimerization loss of tetracycline HCl upon preparation of the Topicycline solution. Percent TC.HCl. retention then was calculated based upon the initial assay value found upon preparation of the solution. This value was found to be 2.79 mg./ml., hence the calculations were carried out as follows: assay value in mg./ml./initial assay value in mg./ml. × 100 = Percentage of TC.HCl retained.

It can thus be seen from the above data that the compositions of the present invention are considerably more stable on extended storage than a typical prior art composition.

What is claimed is:

1. A stable nonaqueous solution of tetracycline hydrochloride consisting essentially of a mixture of 0.25 to 2 percent tetracycline hydrochloride, 41 to 88 percent of a nonaqueous diluent material selected from the class consisting of glyceryl triacetate, diisopropyl sebacate, diisopropyl adipate, isopropyl palmitate, isopropyl myristate, lauryl lactate, linear alcohol lactate, decyl oleate, isodecyl oleate, 2-ethylhexyl palmitate, isopropyl linoleate, acetylated monoglyceride, acetyl tributyl citrate, acetyl triethyl citrate, tricyclo hexyl citrate, butyl myristate, promyristyl propionate, dibutyl sebacate, dioctyl adipate, dioctyl succinate, isobutyl acetate, acetamide, methyl acetamide, polydimethyl cyclosiloxane, hexamethyl disiloxane, and fractionated triglycerides of coconut oil origin, 4 to 40 percent of a nonaqueous solvent selected from the class consisting of ethanol, methanol, isopropanol, butanol, N-methyl-2-pyrrolidone and acetone, 0.3 to 20 percent nonaqueous nonionic solubilizer selected from the class consisting of polyethylene glycols, methoxy polyethylene glycols, polysorbates, ethylene oxide-propylene oxide block copolymers, sorbitan esters and glycerin, 0 to 6 percent nonaqueous anionic solubilizer selected from the class consisting of monovalent or divalent salts of dialkyl sulfosuccinates, acyl lactates and aryl sulfonates, and 0 to 0.75 percent antioxidant selected from the class consisting of ascorbyl palmitate, ascorbic acid, propyl gallate, butylated hydroxytoluene, butylated hydroxyanisole, tertiary butyl hydroquinone, and d-beta, gamma and delta isomers of tocopherol, said percent values being on a weight/weight basis based on the entire solution weight.

2. A stable solution according to claim 1 wherein the components are present in the amounts of 0.3 to 1.5 percent tetracycline hydrochloride, 57 to 84 percent nonaqueous diluent, 4 to 30 percent nonaqueous solvent, 2 to 9 percent nonaqueous nonionic solubilizer, 1 to 6 percent nonaqueous anionic solubilizer and 0.03 to 0.2 percent antioxidant.

3. A stable solution according to claim 1 wherein the components are present in the amounts of 0.5 to 1.25 percent tetracycline hydrochloride, 60 to 81 percent nonaqueous diluent, 4 to 25 percent nonaqueous solvent, 3 to 9 percent nonaqueous nonionic solubilizer, 1.5 to 4.5 percent nonaqueous anionic solubilizer and 0.1 to 0.2 percent antioxidant.

* * * * *